United States Patent
Dannar et al.

(10) Patent No.: US 8,479,813 B2
(45) Date of Patent: Jul. 9, 2013

(54) BIOGENIC FUEL GAS GENERATION IN GEOLOGIC HYDROCARBON DEPOSITS

(75) Inventors: Verlin Dannar, Sheridan, WY (US); Robert S. Pfeiffer, Parker, CO (US); Roland P. DeBruyn, Highlands Ranch, CO (US); Shane Bower, Golden, CO (US); Glenn A. Ulrich, Rolla, MO (US); Jeffrey L. Weber, Denver, CO (US); David Brock, Littleton, CO (US); Jim Ford, Gillette, WY (US); Travis Meyers, Gillette, WY (US); Mark Finkelstein, Morrison, CO (US)

(73) Assignee: LUCA Technologies, Inc., Golden, CO (US)

( * ) Notice: Subject to any disclaimer, the term of this patent is extended or adjusted under 35 U.S.C. 154(b) by 860 days.

(21) Appl. No.: 12/639,483

(22) Filed: Dec. 16, 2009

(65) Prior Publication Data
US 2011/0139439 A1 Jun. 16, 2011

(51) Int. Cl.
*E21B 43/22* (2006.01)

(52) U.S. Cl.
USPC .................................. 166/246; 166/305.1

(58) Field of Classification Search
None
See application file for complete search history.

(56) References Cited

U.S. PATENT DOCUMENTS

| | | |
|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 2,185,216 A | 5/1965 | Hitzman |
| 3,185,216 A | 5/1965 | Hitzman |
| 3,332,487 A | 7/1967 | Jones |
| 3,340,930 A | 9/1967 | Hitzman |
| 3,437,654 A | 4/1969 | Dix |
| 3,637,686 A | 1/1972 | Kokubo et al. |

(Continued)

FOREIGN PATENT DOCUMENTS

| | | |
|---|---|---|
| DE | 4036787 B1 | 5/1992 |
| DE | 4115435 B2 | 8/1992 |

(Continued)

OTHER PUBLICATIONS

European Examination Report of EP 05 745 350.8 mailed Mar. 14, 2011, 8 pages.

(Continued)

*Primary Examiner* — Zakiya W Bates
(74) *Attorney, Agent, or Firm* — Kilpatrick Townsend & Stockton LLP

(57) ABSTRACT

Methods to enhance biogenic gas production in an anaerobic geologic formation containing carbonaceous material may include the steps of accessing the anaerobic formation, increasing a rate of production of the biogenic gases in the anaerobic formation, and flowing formation water within the anaerobic formation after the increase in the production of biogenic gases. Methods to redistribute formation water in an anaerobic geologic formation containing carbonaceous material may include the steps of locating a reservoir of the formation water within the anaerobic formation, forming at least one channel between the reservoir and at least a portion of the carbonaceous material, and transporting the formation water from the reservoir to the carbonaceous material through the channel. The methods may also include the accumulation of biogenic gas in an anaerobic geologic formation to enhance biogenic gas production.

26 Claims, 6 Drawing Sheets

U.S. PATENT DOCUMENTS

| | | | |
|---|---|---|---|
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wilberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,648,458 A | 3/1987 | Broadus |
| 4,666,605 A | 5/1987 | Minami et al. |
| 4,678,033 A | 7/1987 | Killough |
| 4,799,545 A | 1/1989 | Silver et al. |
| 4,826,769 A | 5/1989 | Menger |
| 4,845,034 A | 7/1989 | Menger et al. |
| 4,883,753 A | 11/1989 | Belaich et al. |
| 4,905,761 A | 3/1990 | Bryant |
| 4,906,575 A | 3/1990 | Silver et al. |
| 4,914,024 A | 4/1990 | Strandberg et al. |
| 4,947,932 A | 8/1990 | Silver et al. |
| 4,971,151 A | 11/1990 | Sheehy |
| 5,044,435 A | 9/1991 | Sperl et al. |
| 5,076,927 A | 12/1991 | Hunter |
| 5,083,610 A | 1/1992 | Sheehy |
| 5,083,611 A | 1/1992 | Clark et al. |
| 5,087,558 A | 2/1992 | Webster, Jr. |
| 5,100,553 A | 3/1992 | Nomura et al. |
| 5,163,510 A | 11/1992 | Sunde |
| 5,297,625 A | 3/1994 | Premuzic et al. |
| 5,327,967 A | 7/1994 | Jenneman et al. |
| 5,340,376 A | 8/1994 | Cunningham |
| 5,341,875 A | 8/1994 | Jenneman et al. |
| 5,350,684 A | 9/1994 | Nakatsugawa et al. |
| 5,360,064 A | 11/1994 | Jenneman et al. |
| 5,363,913 A | 11/1994 | Jenneman et al. |
| 5,368,099 A | 11/1994 | Davey et al. |
| 5,424,195 A | 6/1995 | Volkwein |
| 5,490,634 A | 2/1996 | Jain et al. |
| 5,492,828 A | 2/1996 | Premuzic et al. |
| 5,500,123 A | 3/1996 | Srivastava |
| 5,510,033 A | 4/1996 | Ensley et al. |
| 5,516,971 A | 5/1996 | Hurley |
| 5,538,530 A | 7/1996 | Heaton et al. |
| 5,551,515 A | 9/1996 | Fodge et al. |
| 5,560,737 A | 10/1996 | Schuring et al. |
| 5,593,886 A | 1/1997 | Gaddy |
| 5,597,730 A | 1/1997 | Aust et al. |
| 5,601,700 A | 2/1997 | Bridge et al. |
| 5,630,942 A | 5/1997 | Steiner |
| 5,670,345 A | 9/1997 | Srivastava et al. |
| 5,695,641 A | 12/1997 | Cosulich et al. |
| 5,723,597 A | 3/1998 | Kohne |
| 5,763,736 A | 6/1998 | Daume |
| 5,854,032 A | 12/1998 | Srivastava et al. |
| 5,858,766 A | 1/1999 | Premuzic et al. |
| 5,885,825 A | 3/1999 | Lin et al. |
| 5,919,696 A | 7/1999 | Ikeda et al. |
| 5,928,864 A | 7/1999 | Kohne |
| 5,955,261 A | 9/1999 | Kohne |
| 5,955,262 A | 9/1999 | Kourilsky et al. |
| 6,090,593 A | 7/2000 | Fleming et al. |
| 6,143,534 A | 11/2000 | Menger et al. |
| 6,202,051 B1 | 3/2001 | Woolston |
| 6,210,955 B1 | 4/2001 | Hayes |
| 6,265,205 B1 | 7/2001 | Hitchens et al. |
| 6,543,535 B2 | 4/2003 | Converse et al. |
| 6,758,270 B1 | 7/2004 | Sunde et al. |
| 6,795,922 B2 | 9/2004 | Johnson et al. |
| 6,859,880 B2 | 2/2005 | Johnson et al. |
| 7,124,817 B1 | 10/2006 | Sunde |
| 7,426,960 B2 | 9/2008 | Pfeiffer et al. |
| 7,640,978 B2 | 1/2010 | Pfeiffer et al. |
| 7,845,403 B2 | 12/2010 | Pfeiffer et al. |
| 7,975,762 B2 | 7/2011 | Pfeiffer et al. |
| 8,051,908 B2 | 11/2011 | Pfeiffer et al. |
| 2001/0045279 A1 | 11/2001 | Converse et al. |
| 2002/0102673 A1 | 8/2002 | Zhang et al. |
| 2003/0062270 A1 | 4/2003 | McAlister |
| 2003/0205458 A1 | 11/2003 | Roychowdhury |
| 2003/0209340 A1 | 11/2003 | McClung |
| 2003/0216353 A1 | 11/2003 | Mosher et al. |
| 2004/0033557 A1 | 2/2004 | Scott et al. |
| 2004/0035785 A1 | 2/2004 | Rebholz |
| 2004/0164971 A1 | 8/2004 | Hayward et al. |
| 2005/0053955 A1 | 3/2005 | Sowlay et al. |
| 2005/0205260 A1 | 9/2005 | McClung, III |
| 2006/0223153 A1 | 10/2006 | Pfeiffer |
| 2006/0254765 A1 | 11/2006 | Pfeiffer et al. |
| 2007/0092930 A1 | 4/2007 | Lal et al. |
| 2008/0289816 A1 | 11/2008 | Pfeiffer et al. |
| 2008/0299635 A1 | 12/2008 | Pfeiffer et al. |
| 2010/0101782 A1 | 4/2010 | Pfeiffer et al. |
| 2010/0300680 A1 | 12/2010 | Pfeiffer et al. |
| 2011/0284215 A1 | 11/2011 | Pfeiffer et al. |

FOREIGN PATENT DOCUMENTS

| | | |
|---|---|---|
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 B6 | 9/2001 |
| WO | WO 02/34931 A2 | 5/2002 |
| WO | WO 2005/115649 A1 | 12/2005 |
| WO | WO 2006/118570 A1 | 11/2006 |

OTHER PUBLICATIONS

Ulrich, Glenn A. et al., "Active Biogenesis", Energy, Spring 2005, XP008128250, pp. 21-26.

Aitken, Carolyn M. et al "Anaerobic hydrocarbon degradation in deep subsurface oil reserves" Nature, Sep. 16, 2004, pp. 291-294.

Anderson, Robert T., and Lovley, Derek R., "Hexadecane Decay by Methanogenesis", Nature, v. 404, p. 722, Apr. 13, 2000.

Anderson, Robert T., Rooney-Varga, Juliette N., et al., "Anaerobic Benzene Oxidation in the Fe(III) Reduction Zone of Petroleum-Contaminated Aquifers", Environmental Science & Technology, v. 32, pp. 1222-1229, 1998.

Artech Inc., Biological Gasification of Coals. Final Report, U.S. Department of Energy, Contract DE-AC21-87MC23285, pp. 40-63, 1990.

Basiliko, Nathan et al. "Influence of Ni, Co, Fe, and Na additions on methane production in Sphagnum dominated Northern American peatlands" Biogeochemistry, 2001, 52: 133-153.

Belyaev, S. S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Bernard, F. P., et al. "Indigenous Microorganisms in Connate Water of Many Oil Fields: A New Tool in Exploration and Production Techniques" SPE 24811, 1992, pp. 467-476.

Boone, David R. et al., Bergey's Manual of Systematic Bacteriology—Second Edition—vol. One "The Archaea and the Deeply Branching and Phototrophic Bacteria", Springer, 4 pages.

Brockman, Fred "Regulation of Microbial Communities" at http://www.sysbio.org/sysbio/microbial/index.stm, 2005, 2 pages.

Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Cervantes, Francisco J. et al, "Competition between methanogenesis and quinone respiration for ecologically important substrates in anaerobic consortia" FEMS Microbiology Ecology 34, 2000, pp. 161-171.

Claypool, George E. et al. "The Origin and Distribution of Methane in Marine Sediments" Natural Gases in Marine Sediments, Ed. Isaac R. Kaplan, 1974, pp. 99-139.

Claypool, Geroge E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.

Clayton et al. "Oil-Generating Coals of the San Juan Basin, New Mexico and Colorado, U.S." Org. Geochem. 1991, pp. 735-742, vol. 17, No. 6.

Clayton, C. et al. "Source Volumetrics of Biogenic Gas Generation" Bacterial Gas, Ed. R. Vially, 1992, pp. 191-204, Paris.

Coates, John D., Anderson, Robert T., et al., "Anaerobic Hydrocarbon Degradation in Petroleum-Contaminated Harbor Sediments under Sulfate-Reducing and Artificially Imposed Conditions", Environ. Sci. Technol., vol. 30, No. 9, pp. 2784-2789, 1996.

Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.

Connan, J. et al. "Origin of Gases in Reservoirs" 1995 International Gas Research Conference, 1996, pp. 21-41.

Conrad, R. "Contribution of hydrogen to methane production and control of hydrogen concentrations in methanogenic soils and sediments" FEMS Microbiology Ecology, 28 (1999) pp. 193-202.

DeBruin, R.H. et al. "Coalbed Methane in Wyoming" Wyoming State Geological Survey (Laramie, WY), Information Pamphlet 7 (second revision), 2004, 24 pages.

Donaldson et al., "Conference Focuses on Microbial Enhancement of Oil Recovery," The Oil and Gas Journal, pp. 47-52, Dec. 20, 1982.

Donaldson, Eric C. et al. Microbial Enhanced Oil Recovery, Developments in Petroleum Science, 1989, v. 22, pp. 1-14, 121, 123, 149, Elsevier.

Faber, E. et al. "Distinction of Bacterial and Thermogenic Hydrocarbon Gases" Bacterial Gas, Ed. R. Vially, 1992, pp. 63-74, Paris.

Flesner, R. et al. "Pilot-scale base hydrolysis processing of HMX-based plastic-bonded explosives", 4th International Symposium on Special Topics in Chemical Propulsion: Challenges in Propellants and 100 Years After Nobel, May 27-31, 1996, pp. 213-220.

Flesner, R. et al. "Pilot-scale base hydrolysis processing of HMX-based plastic-bonded explosives", Chemical Abstracts, vol. 130, No. 5, Feb. 1, 1998, Columbus, Ohio, U.S.; Abstract No. 54464a, pp. 835.

Gaasterland, Terry "Archaeal Genomics" Current Opinions in Microbiology (1999) 2:542-547.

Galagan, James, E. et al. "The Genome of M. acetivorans Reveals Extensive Metabolic and Physiological Diversity" Genome Research 12: 532-542 (2002).

Grbic-Galic, D., and Vogel, T. "Transformation of Toluene and Benzene by mixed methanogenic cultures" Applied and Environmental Microbiology, 1987, v. 53, pp. 254-260.

Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.

Gullapalli, Irene L. et al., "Laboratory Design and Field Implementation of Microbial Profile Modification Process", SPE Reservoir Evaluation & Engineering, v. 3, No. 1, pp. 42-49, Feb. 2000.

Halbouty, M.T. "East Texas Field—USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.

Hales, B.A. et al. "Isolation and Identification of Methanogen-specific DNA from Blanket Bog Peat by PCR Amplification and Sequence Analysis", Applied and Environmental Microbiology, 1996, pp. 668-675.

Hattori, Satoshi et al.; "Thermacetogenium phaeum gen.nov.,sp.nov., a strictly anaerobic, thermophilic, syntrophic acetate-oxidizing bacterium", Internation. Journal of Systematic and Evolutionary Microbiology (2000), 50, 1601-1609, 9 pages, 2000.

Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.

Hunkeler et al., "Petroleum Hydrocarbon Mineralization in Anaerobic Laboratory Aquifer Columns," Journal of Contaminant Hydrology 32, pp. 41-61, 1998.

Ivanov, M. V. et al. "Additional Oil Production During Field Trials in Russia: Microbial Enhancement of Oil Recovery—Recent Advances" (4th US DOE MEOR Int Conf (Upton, NY, 1992) Proc; Elsevier Develop Petrol Sci Ser No. 39), 1993, pp. 373-381.

Ivanov, M. V. et al. "Die mikrobiologische Bildung von Methan in einer abzubauenden Erdollagerstatte" Frieberger Forschungshefte Reihe C, v., 1982, vol. 389, pp. 189-199.

Johnson et al., 1991, "Preliminary Results of a Coalbed Methane Assessment of the Wind River Indian Reservation, Whoming" Coalbed Methane, pp. 273-284.

Johnson, Ronald C. et al. "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.

Kasting, James F. "When Methane Made Climate" Scientific American, Jul. 2004, pp. 80-85.

Kim, Ann G. "Experimental Studies on the Origin and Accumulation of Coalbed Gas" U.S. Dept. of the Interior Bureau of Mines, Report of Investigations 8317, 1978, 18 pages.

Kim, Ann G. et al. "Hydrocarbon Gases Produced in a Simulated Swamp Environment" U.S. Dept. of the Interior Bureau of Mines, Report of Investigations 7690, 1972, 13 pages.

Klein, A. et al. "Comparative Analysis of Genes Encoding Methyl Coenzyme M Reductase in Methanogenic Bacteria", Mol Gen Genet, 1988, 213:409-420.

Krumholtz, Lee R. et al. "Confined subsurface microbial communities in Cretaceous Rock" Nature (Mar. 6, 1997) pp. 64-66.

Kunzig, Robert "20,000 Microbes Under the Sea" Mar. 2004, pp. 32-41 , vol. 25, No. 3.

Law, Ben E. et al "Coalbed Gas Accumulations in the Paleocene Fort Union Formation, Powder River Basin, Wyoming" Coalbed Methane—1991; Rocky Mountain Association of Geologists, pp. 179-190.

Le Blanc, Leonard, Artificial Recharge, Offshore, p. 10, Feb. 2000.

L'Haridon, S., Reysenbach, A.L., et al., Hot Subterranean Biosphere in a Continental Oil Reservoir, Nature, v. 377, pp. 223-224, Sep. 21, 1995.

Li, M. et al. "Advances in Simulated Tests of Biogas" Oil & Gas Geology, 1996, v. vol. 17, No. 2, pp. 117-122, with abstract.

Lollar, B. Sherwood et al. "Evidence for bacterially generated hydrocarbon gas in Canadian Shield and Fennoscandian Shield rocks" Geochemicaet Cosmochimica Acta vol. 57, pp. 5073-5085 (1993).

Lomans, Bart P. et al. "Isolation and Characterization of *Mehanomethylovorans hollandica* gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.

Lovely, Derek R. "Deep Subsurface Microbial Processes" Reviews of Geophysics, 33, 3 / Aug. 1995, pp. 365-381.

Luca Technologies, "Tatums—Laboratory Testing," received by the European Patent Office May 14, 2010, 2 pages.

Magot, Michel et al. "Microbiology of Petroleum Reservoirs" Antonie van Leeuwenhoek, 2000, 77: 103-116.

Mattavelli, L. et al. "Deep Isotopic Light Methane in Northern Italy" Bacterial Gas, Ed. R. Vially, 1992, pp. 121-132.

McDonald, I.R. et al. "Molecular Ecological Analysis of Methanogens and Methanotrophs in Blanket Bog Peat" Microbial Ecology (1999) 38:225-233.

Nandi, R et al. "Microbial Production of Hydrogen: An Overview" Critical Reviews in Microbiology, 24 (1): 61-84 (1998).

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Neue, Heinz-Ulrich "Methane Emission from Rice Fields", BioScience, 1993, pp. 466-473, vol. 43, No. 7, downloaded from http://www.ciesin.org/docs/004-032/004-032.html.

Ng, T. K., and Weimer, P. J., "Possible Nonanthropogenic Origin of Two Methanogenic Isolates from Oil Producing Wells in the San Miguelito Field, Ventura County, California", Geomicrobiology Journal, 1989, v. 7, pp. 185-192. C62.

O'Carroll, Christopher "The Pervasive Presence of Microbes" http://www/umassmag.com/Summer_2003/The_pervasive_presence_of_microbes_5_08.html, 2003, 3 pages.

Orphan et al., "Culture-Dependant and Culture-Independent Characterization of Microbial Assemblages Associated with High-Temperature Petroleum Reservoirs," American Society for Microbiology, pp. 700-711, 2000.

Panow, A. et al. "Mechanisms of Biologically-Mediated Methane Evolution from Black Coal", Fuel Processing Technology v. 52, pp. 115-125, 1997.

Pedersen, K. "Exploration of Deep Intraterrestrial Microbial Life: Current Perspectives" FEMS Microbiology Letters 185 (2000) pp. 9-16.

Potter et al. "Artificial Recharge," Offshore, Feb. 2000, pp. 10.

Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.

Reeve, John N. "Archaebacteria Then . . . Archaes Now (Are There Really No Archaeal Pathogens?)" Journal of Bacteriology, vol. 181, No. 12, Jun. 1999 pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resource potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981.

Rice, Dudley D. et al. "Identification and Significance of Coal-Bed Gas, San Juan Basin, Northwestern New Mexico and Southwestern Colorado" Geology and Coal-Bed Methane Resources of the Northern San Juan Basin, Colorado and New Mexico, Ed. J. Fassett, Coal-Bed Methane, San Juan Basin, 1988, pp. 51-59, Rocky Mountain Association of Geologists.

Rice, Dudley D. et al. "Nonassociated Gas Potential of San Juan Basin Considerable" Oil & Gas Journal, Aug. 1990, pp. 60-61, vol. 88, No. 33.

Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.

Rightmire, C.T. et al. "Coalbed Methane Resource", 1984, Coalbed methane resources of the United States, AAPG Studies in Geology #17, Tulsa, p. 1-B.

Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.

Rozanova, E.P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995—The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane" International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp. 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Volkwein, J.C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 2004) pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: CO2 reduction vs. acetate fermentation—Isotope evidence" Geochimica et Cosmochimica Acta, 1986, pp. 693-709, vol. 50, No. 5.

Zengler et al., "Methane Formation From Long-Chain Alkanes by Anaerobic Microorganisms," Nature, vol. 401, pp. 266-269, Sep. 16, 1999.

Zobell, C.E., "Bacterial Release of Oil From Sedimentary Materials," The Oil & Gas Journal, pp. 62-65, Aug. 2, 1947.

International Search Report and Written Opinion for PCT Application No. PCT/US05/15259, mailed Mar. 1, 2006, 3 pages.

International Search Report and Written Opinion for PCT Application No. PCT/US07/02420, mailed Jan. 4, 2008, 4 pages.

International Search Report and Written Opinion for PCT Application No. PCT/US05/15188, mailed Nov. 15, 2005, 2 pages.

PCT International Search Report and Written Opinion mailed Nov. 5, 2010; International Application No. PCT/US2010/049845; 14 pages.

BIOGENIC FUEL GAS GENERATION IN GEOLOGIC HYDROCARBON DEPOSITS

CROSS-REFERENCES TO RELATED APPLICATIONS

This application is related to U.S. application Ser. No. 12/129,441, filed May 29, 2008, which was a continuation of U.S. application Ser. No. 11/343,429, filed Jan. 30, 2006, which was a continuation-in-part of International Application PCT/US2005/015259, with an international filing date of May 3, 2005. The entire contents of all the above-identified applications are herein incorporated by this reference for all purposes.

BACKGROUND OF THE INVENTION

The formation water present in subterranean geologic formations of oil, coal, and other carbonaceous materials is normally considered an obstacle to the recovery of materials from those formations. In coal mining, for example, formation water often has to be pumped out of the formation and into remote ponds to make the coal accessible to mining equipment. Similarly, formation water has to be separated from the crude oil extracted from a subterranean field and disposed of typically underground. The extraction, separation and disposal of the formation water add costs to recovery processes, and generate a by-product regarded as having little value.

Further investigation, however, has revealed that even extracted formation water can support active communities of microorganisms from the formation. The presence of these microorganisms in the formation environment were known from previous recovery applications, such as microbially enhanced oil recovery (MEOR), where the microorganisms naturally generate surface active agents, such as glycolipids, that help release oil trapped in porous substrates. In MEOR applications, however. it was generally believed that the microorganisms were concentrated in a boundary layer between the oil and water phases. The bulk formation water was believed to be relatively unpopulated, because it lacked the proper nutrients for the microorganisms. More recent studies have shown that robust populations of microorganisms do exist in the bulk formation water, and can even survive extraction from the geologic formation under proper conditions.

The discovery of active populations of microorganisms in bulk formation water has come at a time when new applications are being envisioned for these microorganisms. For years, energy producers have seen evidence that materials like methane are being produced biogenically in formations, presumably by microorganisms metabolizing carbonaceous substrates. Until recently, these observations have been little more than an academic curiosity, as commercial production efforts have focused mainly on the recovery of coal, oil, and other fossil fuels. However, as supplies of easily recoverable natural gas and oil continue to dwindle, and interest grows using more environmentally friendly fuels like hydrogen and methane, biogenic production methods for producing these fuels are starting to receive increased attention.

Unfortunately, the techniques and infrastructure that have been developed over the past century for energy production (e.g., oil and gas drilling, coal mining, etc.) may not be easily adaptable to commercial-scale, biogenic fuel production. Conventional methods and systems for extracting formation water from a subterranean formation have focused on getting the water out quickly, and at the lowest cost. This is particularly evident in coal bed methane (CBM) production. Little consideration has been given to extracting the water in ways that preserve the microorganisms living in the water, or preserve the water resource. Similarly, there has been little development of methods and systems to harness microbially active formation water for enhancing biogenic production of hydrogen, methane, and other metabolic products of the microbial digestion of carbonaceous substrates. Thus, there is a need for new methods and systems of extracting, treating, and transporting formation water within, between, and/or back into geologic formations, such that microbial activity in the water can be preserved and even enhanced.

New techniques are also needed for stimulating microorganisms to produce more biogenic gases. Native consortia of hydrocarbon consuming microorganisms usually include many different species that can employ many different metabolic pathways. If the environment of a consortium is changed in the right way, it may be possible to change the relative populations of the consortium members to favor more combustible gas production. It may also be possible to influence the preferred metabolic pathways of the consortium members to favor combustible eases as the metabolic end products. Thus, there is also a need for processes that can change a formation environment to stimulate a consortium of microorganisms to produce more combustible biogenic gases.

BRIEF SUMMARY OF THE INVENTION

Methods are described for flowing aqueous liquids, such as formation water, through carbonaceous materials inside anaerobic geologic formations. The flowing liquid may have functions analogous to a circulatory system in a living organism by delivering nutrients and removing wastes from microorganisms in contact with the flowing fluid. The flowing liquid may also function as a transport mechanism that disperses the microorganisms to new areas of carbonaceous material, which can increase both their rate of population growth and biogenic gas production. These methods may include inducing fluid flow events on a regular or semi-regular basis in the anaerobic formation to maintain or increase the rate of biogenic gas production. The fluid for these fluid flow events may be provided by an external fluid source introduced to the formation, or fluid already present in the formation (e.g., formation water).

Embodiments of the invention include methods to enhance biogenic gas production in an anaerobic geologic formation containing carbonaceous material. The methods may include the step of accessing the anaerobic formation. They may also include increasing a rate of production of the biogenic gases in the anaerobic formation, and flowing formation water within the anaerobic formation after the increase in the production of biogenic gases.

Embodiments of the invention also include methods to redistribute formation water in an anaerobic geologic formation containing carbonaceous material. The methods may include the step of locating a reservoir of the formation water within the anaerobic formation. The methods may further include forming at least one channel between the reservoir of formation water and at least a portion of the carbonaceous material, and transporting the formation water from the reservoir to the carbonaceous material through the channel.

Embodiments of the invention further include methods of accumulating biogenic gas in an anaerobic geologic formation to enhance biogenic gas production. The methods may include the step of holding the accumulating biogenic gas in the anaerobic formation to increase gas pressure in at least a part of the anaerobic formation. The methods may also include driving formation water through carbonaceous material in the anaerobic formation in response to the increased gas pressure. The flow of the formation water through the carbonaceous material may further increase the rate of biogenic gas production in the anaerobic formation.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

There is increasing evidence that the circulation of water in an anaerobic geologic formation increases the rate of biogenic gas production in the formation. While the water itself may not be a nutrient or activation agent for microorganisms producing the gas, the properties of flowing water as a transport medium for nutrients, activation agents and other compounds, as well as a transport medium for the dispersal of microorganisms, plays a role in enhancing biogenic gas production. Flowing water may also help carry away and dilute the waste products and other compounds that may have an inhibitory effect on microorganism grown and metabolic rates.

The source of the flowing water may come from outside the anaerobic formation, or may be found within the formation. Sources outside the formation may include treated water transported to the formation, and formation waters supplied from one or more separate geologic formations. Sources within the formation may include reservoirs of formation water inside the anaerobic formation that have limited or no contact with carbonaceous material that can provide a nutrient substrate for methanogenic microorganisms.

Figure 1A:
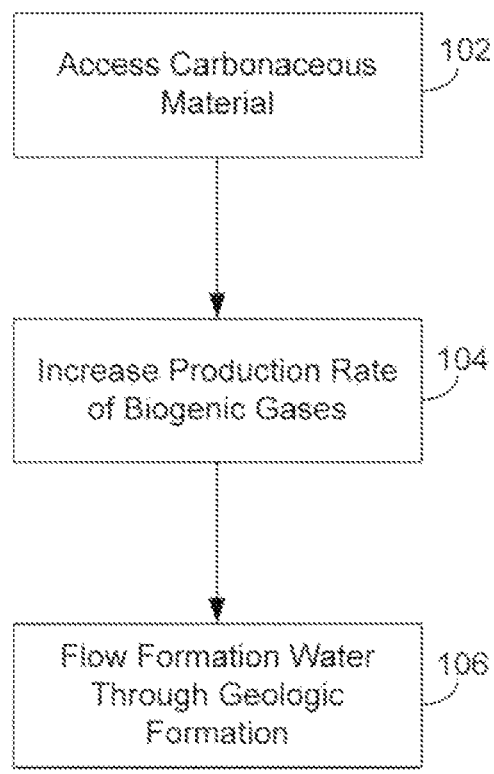
FIGS. 1A-B show flowcharts with selected steps in methods of enhancing biogenic gas production according to embodiments of the invention.

Referring now to FIG. 1A, selected steps in methods 100 of enhancing biogenic gas production according to embodiments of the invention are shown. The methods 100 may include the step of accessing carbonaceous material 102 in an anaerobic geologic formation. The carbonaceous material may include bituminous coal, subbituminous coal, anthracite, oil, carbonaceous shale, oil shale, tar sands, tar, lignite, kerogen, bitumen, and peat, among other carbonaceous materials. The anaerobic geologic formation that holds the carbonaceous material may be a previously explored formation such as a coal field, oil field, natural gas deposit, or carbonaceous shale deposit, among other formations. In many instances, the formation may be accessed through previously mined or drilled access points used to recover carbonaceous material. For previously unexplored formations, access may involve digging or drilling through a surface layer to access an underlying site containing carbonaceous material.

The geologic formation may be a subterranean anaerobic formation. Because sub-surface formation environments typically contain less free atmospheric oxygen (e.g. $O_2$) than found in tropospheric air, the formation environment may be described as anaerobic. These anaerobic formation environments may support microorganisms that can live and grow in an atmosphere having less free oxygen than tropospheric air (e.g., less than about 18% free oxygen by mol.). In some instances, microorganisms may operate in a low oxygen atmosphere, where the 0, concentration is less than about 10% by mol., or less than about 5% by mol., or less than about 2% by mol., or less than about 0.5% by mol.

Once the anaerobic formation has been accessed, actions may be taken to increase the production rate of biogenic gases 104 in the formation. These actions may include introducing a chemical amendment or nutrient to the formation, such as an acetate-containing compound. a phosphorous-containing compound, a yeast extract, a hydrogen-containing compound (e.g., $H_2$), among other compounds and combinations of compounds. These actions may also include introducing a consortium of microorganism's to the formation, such as a consortium capable of anaerobic biogenic gas production (e.g., methanogenesis). These actions may further include introducing water to the anaerobic formation.

Following an action to increase the production rate of biogenic activity, the rate of biogenic gas production may be measured to determine if the action was successful in increasing the production rate. For example, recovery rates for natural gas (e.g., methane and/or other light hydrocarbons) at a wellhead having access to the formation may be measured on a periodic basis (e.g., daily. weekly, monthly, etc.). A significant increase in the recovery rate following the action is indicative of a successful action to increasing the production rate of biogenic gas.

Following the increase in the biogenic gas production rate, formation water may be made to flow within the formation 106. The flowing formation water may maintain or further increase the biogenic gas production rate in the formation. The source of the formation water come from outside the formation, or may come from a reservoir within the formation. Sources of formation water from outside the formation may include formation water supplied from one or more separate formations (e.g., inter-formation transport) and/or formation water extracted and resupplied to the same formation (e.g., intra-formation circulation).

The formation water may be anaerobic formation water. "Anaerobic" formation water is characterized as having little or no dissolved oxygen, in general no more than 4 mg/L, preferably less than 2 mg/L, most preferably less than 0.1 mg/L, as measured at 20° C. and 760 mmHg barometric pressure. During application of the present invention, higher levels of dissolved oxygen, greater than 4 mg/L, can be tolerated without appreciably degrading microorganism performance, for limited times or in certain locations such as a surface layer in a storage or settling tank. Dissolved oxygen can be measured by well-known methods, such as by commercially-available oxygen electrodes, or by the well-known Winkler reaction.

The formation water may also be tested and/or treated to further enhance biogenic gas production. For example, the formation water may be tested to measure properties such as microorganism nutrient levels, pH, salinity, oxidation potential (Eh), and metal ion concentrations, among other properties. An amendment may be added to correct for an imbalance, deficiency, or excess in one or more of these properties. Amendments may also be added that are unprompted by the testing. Formation water treatments may also include filtering and/or processing the reduce the concentration of one or more chemical and/or biological species in the formation water.

Figure 1B:
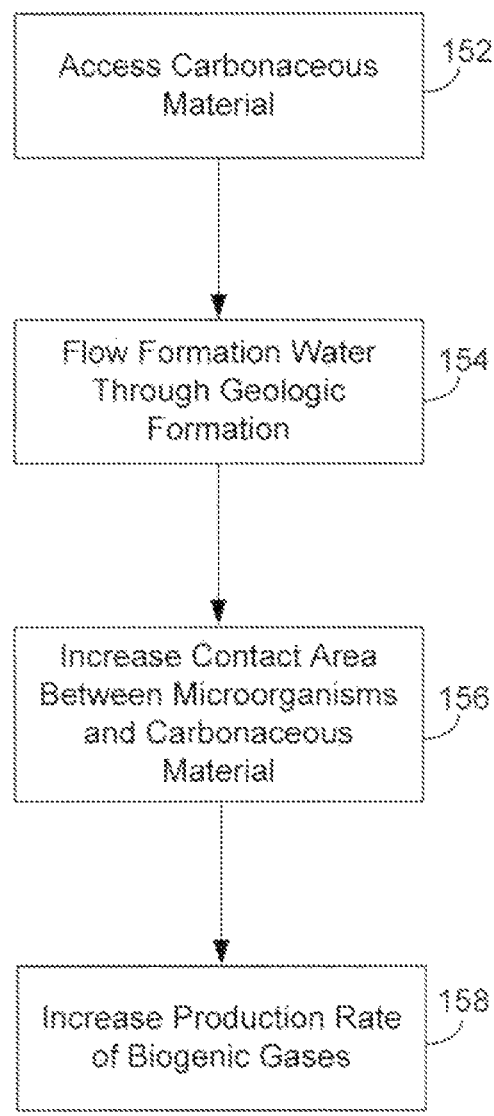

FIG. 1B shows selected steps in methods 150 of enhancing biogenic gas production according to embodiments of the invention. The methods 150 may include the steps of accessing carbonaceous material 152 in an anaerobic geologic formation, and flowing formation water through the formation 154. Flowing the formation water may involve circulating the formation water between a reservoir in the anaerobic formation and carbonaceous material that is also found in the formation. The circulation of the formation water may involve a continuous or near-continuous transportation of water between the reservoir and carbonaceous material. Alternatively, the formation water may be circulated at discontinuous intervals (e.g., periodic intervals) between the reservoir and carbonaceous material. For example, a portion of the reservoir water may be transported to the carbonaceous material over a short period of time, which is followed by a longer period where the formation water stays in contact with the material before returning to the reservoir. At the end of the longer period, the formation water may be recirculated to the carbonaceous material.

As the formation water flows over and/or through the carbonaceous material transports microorganisms, chemical amendments, nutrients, and other materials across a larger volume of the carbonaceous material. This increases the contact area (e.g., surface area) between the carbonaceous material and the migrating microorganisms 156. As the microorganisms are exposed to more nutrients and activators with less crowding from other microorganisms, the rate of production of biogenic gases can start to increase 158. Increased biogenic gas production may also be facilitated by the removal of wastes and other inhibitory substances from the microorganism living environment. When the formation water is circulated on a regular or continuous basis through the carbonaceous material, ability of the circulating water to supply nutrients. disperse microorganisms, and remove wastes can further enhance the rate of biogenic gas production in the formation.

Figure 2:
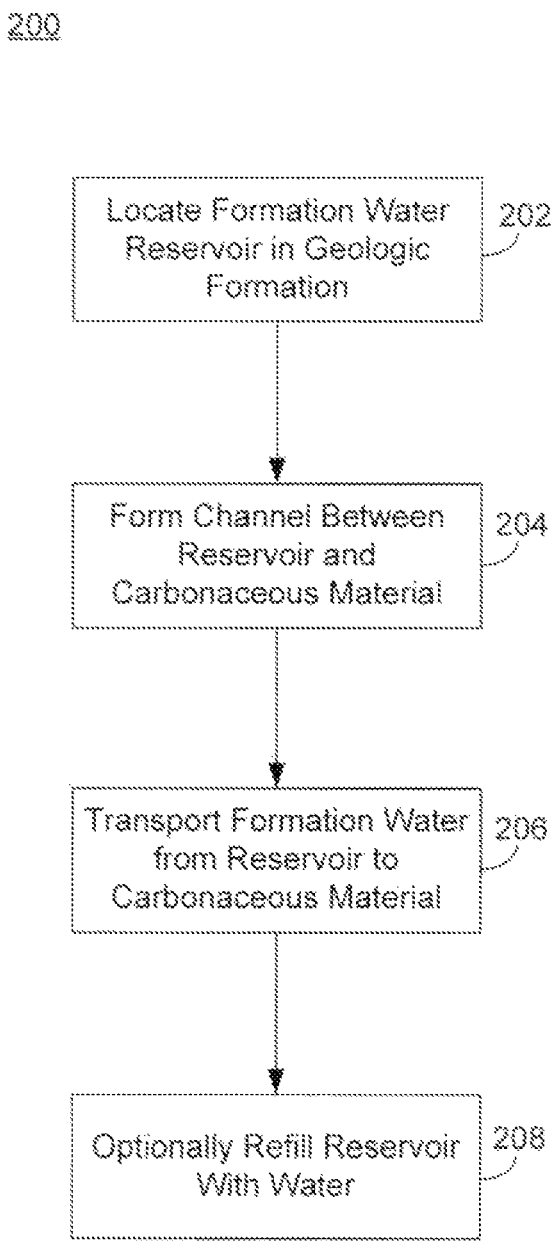
FIG. 2 shows a flowchart with selected steps of in methods of redistributing formation water in anaerobic geologic formations according to embodiments of the invention.

FIG. 2 shows selected steps in methods 200 of redistributing formation water in anaerobic geologic formations according to embodiments of the invention. As noted above, one source of formation water is a reservoir within the anaerobic formation. Methods 200 include the step of locating formation water in such a reservoir in the geologic formation 202. As further described below with reference to FIGS. 3A & 3B, the reservoir may be positioned above or below carbonaceous material in the formation. Alternatively, the reservoir may longitudinally traverse the carbonaceous material such that there may be an upper portion of the reservoir above the carbonaceous material and/or a lower portion of the reservoir below the carbonaceous material.

The formation water reservoir may have little or no fluid contact with targeted carbonaceous material in the formation that may benefit from the flow of the formation water to enhance biogenic methane production. The methods 200 include the step of forming one or more channels between the reservoir and the carbonaceous material 204. The channel may be formed using drilling equipment that drills the channel through a barrier in the formation (e.g., bedrock) that inhibits contact or flow of formation water between the reservoir and carbonaceous material. Alternatively, the harrier may be fractured by mechanical impact or an explosion to form an opening or crack that acts as the channel. The channel can act as a conduit for transporting the formation water from the reservoir to the carbonaceous material 206.

In an optional step, the partially or fully drained reservoir may be refilled by supplying additional water to the reservoir 208. The added water in the reservoir may maintain the transport of the formation water over and/or through the carbonaceous material. The added water may also further distribute microorganisms, nutrients and other materials over a larger volume of the carbonaceous material, as well as allowing these materials to penetrate further into the fractures, cleats, and microchannels of the carbonaceous material. This water may be formation water that is transported from another part of the same geologic formation (i.e., intra-formation transport) or from another formation (i.e., inter-formation transport). The water may also be sourced from outside a geologic formation, such as a surface water source.

Methods are also contemplated for refilling, channels in the formation with water. In some cases, the channels are in fluid communication with a reservoir of formation water. In other cases, the channels are not connected to a reservoir, and may be formed (e.g., drilled) directly into carbonaceous material in the formation. Examples of these channels may further include well bores that were previously used to recover natural gas or other carbonaceous material from the formation. The water used to fill these channels may be formation water, or water from another source.

When a reservoir is located above the carbonaceous material like FIG. 3A below, one or more channels may be formed to permit gravity to transport the reservoir formation water to the underlying carbonaceous material. In this example, the reservoir may be said to be perforated to permit a waterfall of the formation water to flow down (or rain down) on the carbonaceous material. The example may also include transporting the formation water back to the reservoir using a mechanical pump or other pumping means, so the water can re-circulate to the carbonaceous material through the one or more channels.

In another example, the reservoir may be located below the carbonaceous material like FIG. 3B below. The channel may be formed by drilling through the carbonaceous material and barrier between the material and underlying reservoir. The drilling may form one or more channels in the harrier that permits the formation water to be transported through the channel and contact the carbonaceous material. For example, a plurality of channels may be formed, and at least one channel or perforation may be coupled to a source of pressure that can force formation water through the other channels to the carbonaceous material. Alternatively, one or more of the channels may be fitted with a mechanical pump to transport water against gravity from the reservoir to the overlying carbonaceous material.

If there is a headspace above the carbonaceous material, the underlying reservoir may be sufficiently pressurized to push the formation water above the carbonaceous material before is showers down on a top surface of the carbonaceous material. The formation water may then be allowed to fall hack down the reservoir before being pumped again over the top of the carbonaceous material.

The methods 200 source and circulate the formation water from within the formation, which can have advantages over supplying the water from outside the formation. Significantly less energy is required to transport the reservoir formation water to the carbonaceous material, than water from outside the formation. Outside water may be pumped and/or trucked over significant distances (e.g., tens to hundreds of miles) before reaching the formation at a substantial expenditure of energy. In addition, an underground reservoir provides a natural storage facility for the formation water that may be difficult and expensive to replicate on the surface. For example, increasingly strict environmental regulations make it difficult to create a water storage pool or reservoir on land, especially if the water is contaminated with hydrocarbons.

Figure 3A:
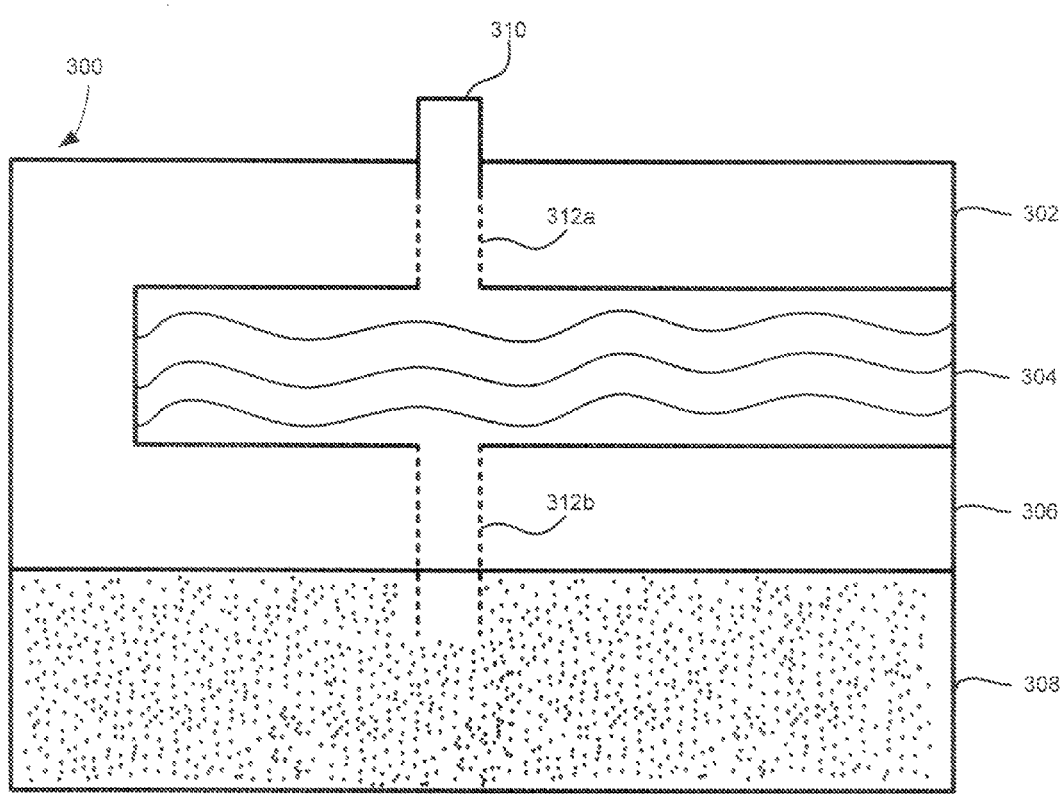
FIGS. 3A & B show simplified cross-sections of a geologic formations containing formation water reservoirs according to embodiments of the inventions.

Referring now to FIG. 3A, a simplified cross-section of a portion of a geologic formation 300 is shown that includes a formation water reservoir 304 positioned above a deposit of carbonaceous material 308. The relative positions of the reservoir 304 and carbonaceous material 308 allow for a gravity fall of the formation water when one or more channels are formed in the layer 306 that separates the reservoir from the carbonaceous material. In FIG. 3A, a channel 312b is shown formed in the layer 306 that provides a way for the formation water to travel from the reservoir 304 to the carbonaceous material 308.

The channel 312b may be formed by drilling through layer 306 until the surface or bulk of the carbonaceous material 308 is reached. This drilling may be a further extension of a well bore 310 that also has a first portion of channel 312a extending from the terrestrial surface of the geologic formation to the top of the formation reservoir 304.

In the embodiment shown in FIG. 3A, a single channel 312b is shown between the reservoir 304 and the carbonaceous material 308. Embodiments may also include a plurality channels (not shown) formed between reservoir 304 and the carbonaceous material 308. The plurality of channels may be said to perforate the reservoir 304 to create a gravity induced fall of formation water onto the carbonaceous material 308.

Figure 3B:
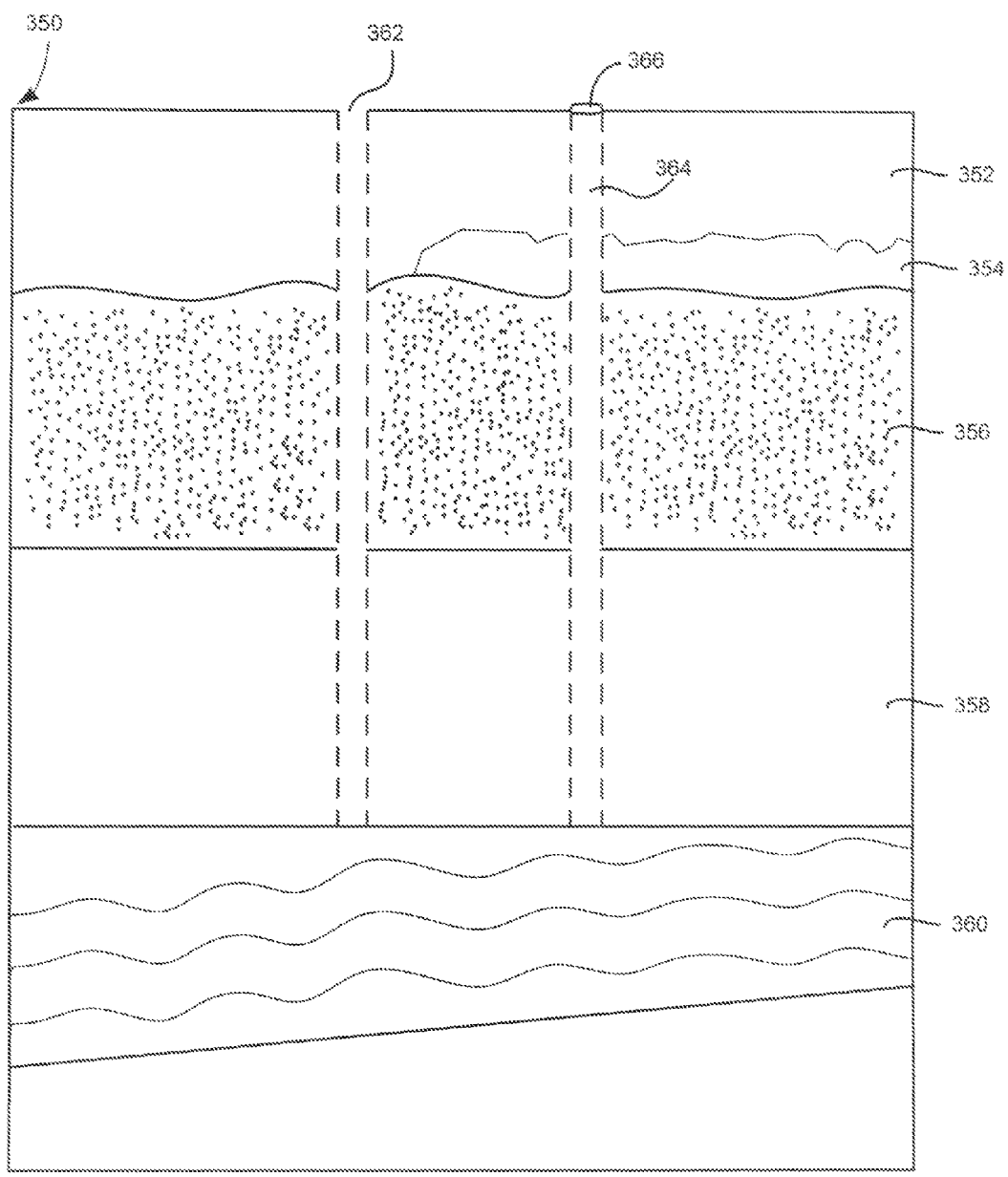

FIG. 3B shows another simplified cross-section of a portion of geologic formation 350 containing a formation water reservoir 360 below a layer of carbonaceous material 356. The reservoir 360 and carbonaceous material 356 are separated by a layer 358 that hinders contact of the underlying formation water with the overlying carbonaceous material. The carbonaceous material 356 is buried underneath layer 352 whose upper surface is the terrestrial surface of the formation 350. One portion of layer 352 is in direct contact with the underlying carbonaceous material 356, while another portion is separated from the carbonaceous material by a pocket 354.

The embodiment shown in FIG. 3B has two channels 362 & 364 formed through several layers of the formation 350, including the layer of carbonaceous material 356 and the layer 358 that separates the reservoir 360 from the carbonaceous material. These channels may be used to transport formation water from the reservoir 360 up to the carbonaceous material 356. For example, channel 362 may be pressurized with a gas or fluid to create an increase in pressure in the formation water in the reservoir 360. This may cause a portion of the formation water to push upwards through channel 366 at least until coming into contact with the carbonaceous material 356. In some embodiments, the formation water may be pushed above the top surface of the carbonaceous material 356 and start filling the pocket 354. As the formation water spills over the top surface of the carbonaceous material 356, it may penetrate and drift down into the material with the aid of gravity.

The top end of channel 364 may include an article 366 to help transport the formation water from the reservoir 360 to the carbonaceous material 356. The article 366 may be a pump or other device to create a negative pressure gradient up the channel 364 that helps to pull the formation water up the channel. Alternatively, the article 366 may be a plug or other device to stop the flow of fluid out of the formation 350. Such a plug may create a positive pressure gradient up the channel 364 that encourages the formation water to flow laterally from the channel into the surrounding formation material, including the carbonaceous material 356.

Figure 4:
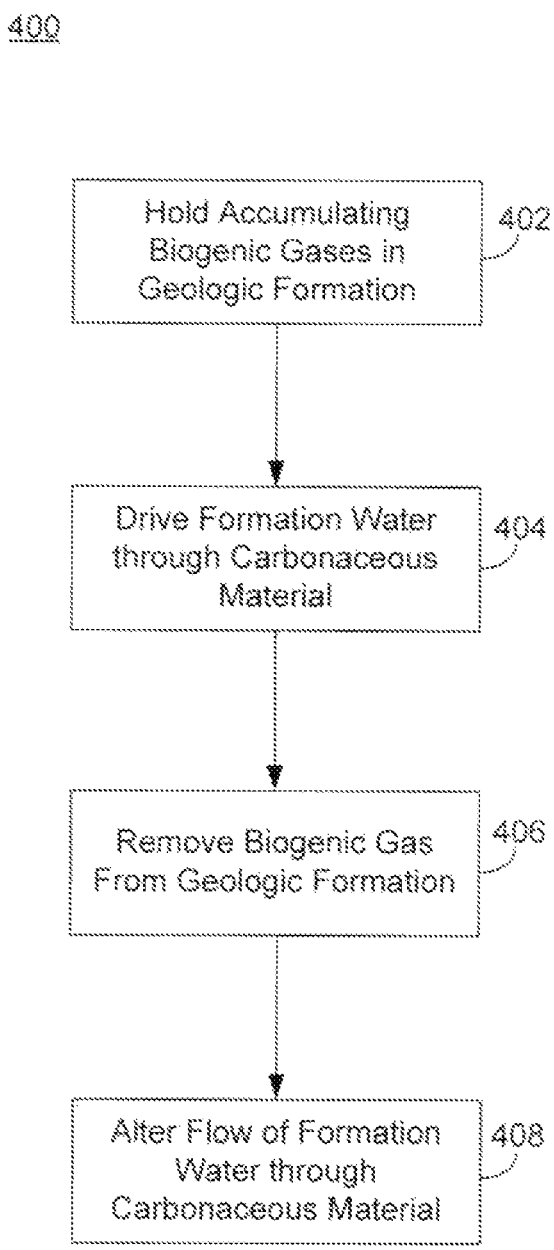
FIG. 4 shows a flowchart with selected steps in methods of accumulating biogenic gas in an anaerobic geologic formation to enhance biogenic gas production according to embodiments of the invention.

Referring now to FIG. 4, methods 400 are described for accumulating biogenic gas in an anaerobic geologic formation to enhance biogenic gas production according to embodiments of the invention. The methods 400 may include the step of holding accumulating biogenic gases in the geologic formation 402. These accumulating gases may be generated native microorganisms in the formation without assistance, and/or by stimulatory actions that start or increase the rate of biogenic gas production in the formation. The accumulating biogenic gas may itself have a stimulatory effect on the rate of biogenic gas production. For example, the gases produced by methanogens, such as methane and hydrogen, may alter the gas'composition of the formation to be more anaerobic, which may facilitate more anaerobic microorganism activity like methanogenesis.

The accumulating biogenic gases held in the formation may also increase the overall gas pressure in the subterranean formation. The increased gas pressure may in turn help drive formation water through carbonaceous material 404. The flow of the formation water through the carbonaceous material may have a stimulatory effect on biogenic gas production (e.g. methanogenesis) which may further increase the rate of biogenic gas production. As noted above, flowing formation water can transport microorganism, nutrients, chemical amendments. and other materials over a wider volume of the carbonaceous materials. The dispersion of the mircoroganims can increase the contact between the microorganisms and the carbonaceous material, which can increase their growth rates and/or biogenic gas production rates. Flowing and/or circulating formation water can also facilitate the removal of microorganism waste products. toxins, and methanogenesis inhibitors from the living environment of the microorganisms.

The ability of increased gas pressure to drive formation water through carbonaceous material may depend on nature of the carbonaceous material and also the composition of the formation. When the carbonaceous material is a relatively porous solid (e.g., lignite coal) the formation water may more easily penetrate into the material. When the carbonaceous material is harder (e.g., anthracite coal) the formation water may have more difficulty penetrating the material, but may still find cracks, fissures, cleats, etc., through which it can traverse the material. In some instances, the carbonaceous material may be sufficiently hard and non-porous that the formation water can only flow around exposed surfaces of the material. For purposes of the present application, driving formation water through the carbonaceous material may include penetrating a porous material, pushing the water further into cracks, fissures, cleats, etc. in the material, and flowing or spreading the water over an exposed surface of the material. In addition, driving formation water through a carbonaceous material does not require the water to be pushed completely through the material. Advancing the formation water into the material or spreading it further across a surface of the material is may also be considered examples of driving the formation water through the material.

In some embodiments of methods 400, at least a portion of the biogenic gases may be removed from the formation 406 following the holding period. For example, these gases may be removed at a wellhead that is fluidly coupled to a natural gas pipeline. The removal of the biogenic gases may cause a change (e.g., decrease) in gas pressure in the formation. A decrease in formation gas pressure may be large enough to alter the flow of formation water through the carbonaceous material 408. In some instances, the decrease in pressure may reverse the direction of flow of the formation water.

Following, the removal of the biogenic gases from the formation, new biogenic gas may be allowed to accumulate in the formation. The accumulating gases held in the formation may cause the gas pressure in the formation to change again (e.g., increase). The gases may be held until the gas pressure reaches a threshold pressure, such as returning to the pressure in the formation prior to the previous release of biogenic gases. An increase in the gas pressure may alter the flow of the formation water again, and in some instances may reverse the direction of flow back to the original flow direction before the biogenic gases were removed. In some embodiments, the removal and re-accumulation of the biogenic gases may be done a plurality of times. This may result in several reversals in the change of the gas pressure in the formation, which may result in corresponding alterations in the direction and/or rate of flow of the formation water through the carbonaceous material. In some instances the removal and re-accumulation of the biogenic gases may result in a cyclical, and possibly continuous, change of flow of the formation water, creating a circulation of the formation water in the carbonaceous material that may enhance biogenic gas production.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the well" includes reference to one or more wells and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method to enhance biogenic gas production in an anaerobic geologic formation containing carbonaceous material, the method comprising:
   accessing the anaerobic formation at specific well locations;
   increasing a rate of production of the biogenic gases in the anaerobic formation; and
   flowing formation water within the anaerobic formation after the increase in the production of biogenic gases, wherein the flowing of formation water comprises circulating the formation water between a native reservoir of the anaerobic formation and the carbonaceous material and back to the native reservoir.

2. The method of claim 1, wherein accumulating biogenic gases are held in the anaerobic formation at specifically designated gas producing wells to increase the rate of production of the biogenic gases.

3. The method of claim 1, wherein the carbonaceous material is contacted with water to increase the rate of production of the biogenic gases.

4. The method of claim 3, wherein the water increases contact between microorganisms and the carbonaceous material in the anaerobic formation.

5. The method of claim 3, wherein the water transports nutrients to microorganisms in the carbonaceous material.

6. The method of claim 3, wherein the water removes inhibitory materials from a living environment of microorganisms in the carbonaceous material, and wherein those inhibitory materials are selected from the group consisting of microorganism waste products, microorganism growth inhibitors, and microorganism methanogenesis inhibitors.

7. The method of claim 3, wherein the water is supplied from a source outside the anaerobic formation, or a reservoir of the formation water within the anaerobic formation.

8. The method of claim 1, wherein an amendment is added to anaerobic formation to increase the rate of production of the biogenic gases.

9. The method of claim 1, wherein the amendment comprises an acetate-containing compound, a phosphorous-containing compound, a yeast extract, or hydrogen.

10. The method of claim 1, wherein the flowing of the formation water comprises pressurizing the anaerobic formation with accumulating biogenic gases at specific gas producing wells to drive formation water through the carbonaceous material while maintaining the preferential gas migration pathways to the gas producing wells.

11. The method of claim 1, wherein the circulating of the formation water further increases the rate of production of biogenic gases.

12. A method to redistribute formation water in an anaerobic geologic formation containing carbonaceous material, the method comprising:
   locating a reservoir of the formation water within the anaerobic formation;
   forming at least one in situ channel to form a direct coupling between the reservoir and at least a portion of the carbonaceous material; and
   directing the formation water from the reservoir to the carbonaceous material through the channel.

13. The method of claim 12, wherein the reservoir is located above or below the carbonaceous material in the anaerobic formation.

14. The method of claim 12, wherein the forming of the channel between the reservoir and the carbonaceous material comprises drilling the channel through formation rock to fluidly connect the reservoir and the carbonaceous material.

15. The method of claim 12, wherein a plurality of channels are formed between the reservoir and the carbonaceous material.

16. The method of claim 12, wherein the transporting of the formation water comprises a gravity flow of the formation water from the reservoir to the carbonaceous material located below.

17. The method of claim 12, wherein the transporting of the formation water comprises showering the formation water on the carbonaceous material from the reservoir located below the carbonaceous material.

18. The method of claim 12, wherein the method further comprises refilling the reservoir with water after the formation water is transported from the reservoir to the carbonaceous material through the channel.

19. The method of claim 18, wherein the water comprises additional formation water.

20. A method of accumulating biogenic gas in an anaerobic geologic formation to enhance biogenic gas production, the method comprising:

holding the accumulating biogenic gas in the anaerobic formation at designated gas producing wells to increase gas pressure in at least a part of the anaerobic formation; and driving formation water through carbonaceous material in the anaerobic formation, wherein the driving is caused by the increased gas pressure, wherein a flow of the formation water through the carbonaceous material occurs due to the connectivity of the gas migration pathways to the gas creating water flow paths further increasing a rate and yield of of biogenic gas production in the anaerobic formation.

21. The method of claim 20, wherein the accumulating biogenic gas is removed from the anaerobic formation after driving the formation water through the carbonaceous material.

22. The method of claim 21, wherein the removal of the accumulating biogenic gas from the anaerobic formation at least partially reverses the flow of the formation water through the carbonaceous material.

23. The method of claim 20, wherein the method comprises removing at least part of the accumulating biogenic gas a plurality of times such that the gas pressure in the anaerobic formation changes over time.

24. The method of claim 23, wherein the changes in gas pressure over time change a direction of the flow of formation water through the carbonaceous material due to the connectivity of the gas migration pathways between the gas producing wells and injection and recovery wells.

25. The method of claim 24, wherein the change in direction of flow further increases the rate, yield, and recovery of biogenic gas production.

26. The method of claim 20, wherein the method comprises:

measuring gas pressure in the anaerobic formation; and removing at least a portion of the accumulating biogenic gas from the anaerobic formation to adjust the gas pressure in the anaerobic formation to a target pressure.

* * * * *